(12) United States Patent
Brown et al.

(10) Patent No.: US 6,790,991 B2
(45) Date of Patent: Sep. 14, 2004

(54) PROCESS FOR THE PREPARATION OF DIPHENYL ETHER COMPOUNDS

(75) Inventors: Stephen Martin Brown, Huddersfield (GB); Brian David Gott, Huddersfield (GB); James Peter Muxworthy, Huddersfield (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/168,611

(22) PCT Filed: Dec. 11, 2000

(86) PCT No.: PCT/GB00/04731

§ 371 (c)(1),
(2), (4) Date: Jun. 20, 2002

(87) PCT Pub. No.: WO01/46130

PCT Pub. Date: Jun. 28, 2001

(65) Prior Publication Data

US 2003/0045754 A1 Mar. 6, 2003

(30) Foreign Application Priority Data

Dec. 22, 1999 (GB) .............................. 9930369

(51) Int. Cl.$^7$ ..................... C07C 303/00; C07C 307/00; C07C 309/00; C07C 311/00; C07C 205/00
(52) U.S. Cl. ......................... 564/99; 562/438
(58) Field of Search ............................ 562/438; 564/99

(56) References Cited

U.S. PATENT DOCUMENTS

| | | | | |
|---|---|---|---|---|
| 4,285,723 A | * | 8/1981 | Cartwright et al. | 71/103 |
| 4,405,805 A | * | 9/1983 | Giacobbe et al. | 560/21 |
| 4,874,846 A | * | 10/1989 | Chene | 534/560 |
| 5,792,888 A | | 8/1998 | Subramanian | 562/857 |
| 6,028,219 A | * | 2/2000 | Atherton et al. | 562/435 |

FOREIGN PATENT DOCUMENTS

| | | |
|---|---|---|
| EP | 274 194 A | 7/1988 |
| GB | 2103214 | 2/1983 |
| GB | 2140417 | 11/1984 |
| WO | 97/10199 | 3/1997 |

OTHER PUBLICATIONS

Xu Jin, "An Exploratory Study of the Synthesis of the Effective Herbicide Fomesafen" Shanghai Huagong, vol. 22(2), pp. 18 22 (1997) Chinese–Language and English Translation.*

Vulakh, E. L. et al, "Use of Phosphorous Oxychloride for the Synthesis of Aromatic Carboxylic Acid Chlorides" Khimicheskaya Promyshlennost (Moscow, Russian Federation), vol. 1, pp. 16–19 (1979)—Caplus Abstract.*

* cited by examiner

Primary Examiner—Richard L. Raymond
Assistant Examiner—Zachary C. Tucker
(74) Attorney, Agent, or Firm—Thomas Hamilton

(57) ABSTRACT

A process for producing fomesafen from acifluorfen comprises the steps of (a) converting acifluorfen to its acid chloride, (b) coupling the acid chloride so formed with methanesulphonamide to form crude fomesafen and (c) purifying the crude fomesafen, characterized in that each of the steps is carried out in a single common solvent, which is preferably a chloroalkane. Preferably the steps are telescoped together so that there is no isolation of the product for any step until fomesafen is obtained.

5 Claims, No Drawings

PROCESS FOR THE PREPARATION OF DIPHENYL ETHER COMPOUNDS

This application is a US National Stage application of International Application No. PCT/GB00/04731 filed Dec. 11, 2000, the contents of which are incorporated herein by reference.

The present invention relates to a process for the production of diphenyl ether compounds which are useful as herbicides. In particular, it relates to a process for obtaining herbicidal diphenyl ether products on an industrial scale.

The problems associated with producing diphenyl ether herbicides on an industrial scale are discussed in WO 97/10200 and WO 97/10199 in which there are disclosed processes for making compounds of formula

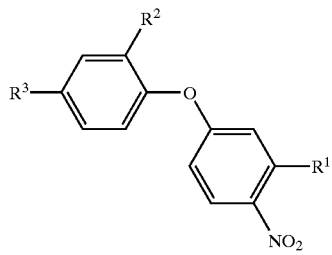

wherein $R^1$ is hydrogen or $C_1$–$C_6$ alkyl, $C_2$–$C_6$ alkenyl or $C_2$–$C_6$ alkynyl (any of which may optionally be substituted with one or more substituents selected from halogen and OH) or COOH, COH, COOR$^4$, COR$^6$, CONR$^4$R$^5$ or CONHSO$_2$R$^4$; $R^4$ and $R^5$ are each independently hydrogen or $C_1$–$C_4$ alkyl optionally substituted with one or more halogen atoms; $R^6$ is a halogen atom or a group $R^4$; $R^2$ is hydrogen or halo; $R^3$ is $C_1$–$C_4$ alkyl, $C_2$–$C_4$ alkenyl or $C_2$–$C_4$ alkynyl, any of which may optionally be substituted with one or more halogen atoms, or halo or, where appropriate, a salt thereof. More especially the disclosures deal with the commercially known herbicides 5-(2-chloro-α,α,α-trifluoro-4-tolyloxy)-2-nitrobenzoic acid (acifluorfen) and 5-(2-chloro-α,α,α-trifluoro-4-tolyloxy)-N-methanesulphonyl-2-nitrobenzamide (fomesafen).

A preferred method of making fomesafen on an industrial scale is via acifluorfen which is made from 5-(2-chloro-α,α,α-trifluoro-4-tolyloxy)-benzoic acid (CTTBA). This compound is produced by oxidation of the corresponding tolyl compound which is in turn obtained from the condensation of 3-hydroxybenzoic acid and 3,4-dichlorobenzotrifluoride.

Because the final product (fomesafen) is required in sufficient purity to meet strict product registration standards the process normally also involves one or more purification procedures.

The synthesis of acifluorfen and its conversion to fomesafen has been the subject of intensive research in an effort to improve one or more of the process steps. Thus for example in WO97/10200 there is disclosed a purification method for acifluorfen or fomesafen, while a set of improved nitration conditions is disclosed in WO97/10199. Another set of possible nitration conditions is disclosed in WO 98/19978. However no processes are known which can perform most or all of the above reactions using a single solvent. This is undoubtedly because the range of reaction conditions is very demanding and it is not at all apparent if a process using a single common solvent is possible.

The applicants have now devised a single common solvent process in which acifluorfen is converted to purified fomesafen. There is therefore provided a process for producing fomesafen from acifluorfen comprising the steps of converting acifluorfen to its acid chloride

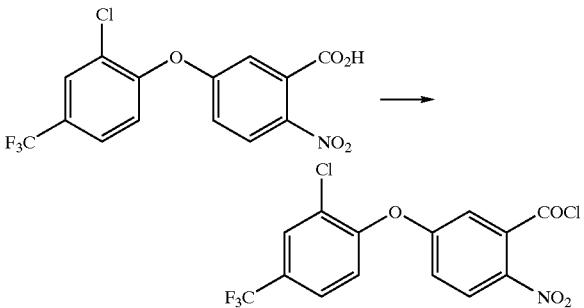

coupling the acid chloride so formed with methanesulphonamide (MSAM) to form crude fomesafen and

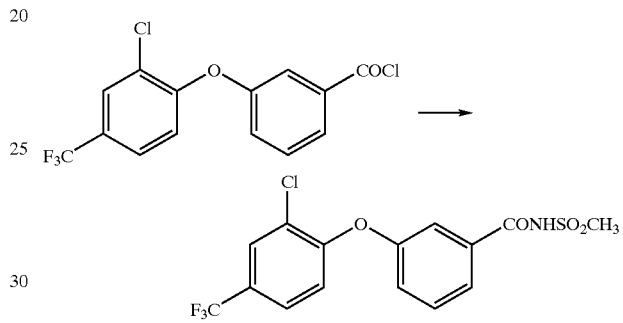

purifying the crude fomesafen characterised in that each of the steps is carried out in a single common solvent.

The product of each step may be isolated at the end of the step or, more preferably, the steps may be telescoped together so that there is no isolation until the purified fomesafen end product is obtained.

Suitable solvents are haloalkanes (such as 1,2-dichloroethane or tetrachloroethylene), halobenzenes (such as fluorobenzene, chlorobenzene and dichlorobenzenes), alkoxybenzenes (such as anisole or phenetole), haloalkylbenzenes (such as benzotrifluoride), and esters (such as ethyl acetate or butyl acetate). Preferred solvents are chloroalkanes especially 1,2-dichloroethane (or ethylene dichloride or EDC).

In a further aspect of the invention the acifluorfen is formed by nitration of

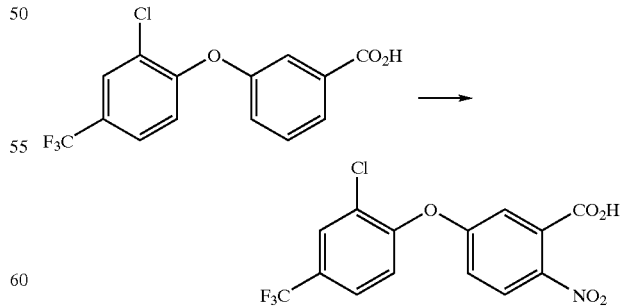

CTTBA in the same solvent used to convert acifluorfen to fomesafen, the solvent being a chloroalkane, especially EDC.

In yet a further aspect of the invention the CTTBA is formed by the oxidation of the corresponding toluene and the CTTBA is extracted from the reaction mass using the same solvent that is used to convert acifluorfen to fomesafen, the solvent being a chloroalkane, especially EDC.

The CTTBA is suitably generated by the oxidation of the corresponding toluene using oxygen together with a catalyst (such as a cobalt or vanadium salt), at a temperature of 70° C. to 150° C.

The product of the extraction step and/or the nitration step may be isolated at the end of the step or, more preferably, the steps may be telescoped together so that there is no isolation of product at the end of each of the extraction and nitration stages.

In one suitable method for the nitration reaction, the nitrating agent may be nitric acid or a mixture of nitric and sulphuric acids although other types of nitrating agent may also be used. It is also advantageous to conduct the reaction in the presence of acetic anhydride and, in this case, it is preferred that the molar ratio of acetic anhydride to CTTBA is from about 1:1 to 3:1. The reaction temperature may be from about −15° to 15° C., more usually from about −10° to 10° C. It is advantageous to add the nitrating agent, over a period of time from 5 to 15 hours, or, more preferably, 6 to 12 hours. Most preferably the reaction is carried out using a mixture of nitric and sulphuric acids at 0–5° C. The resultant product solution is water washed, to remove mineral acid and acetic acid then topped to remove residual water.

The conversion of acifluorfen to the acid chloride may be carried out by conventional methods, for example as set out in EP-A-0003416. It is preferred to perform the reaction with a suitable chlorinating agent such as thionyl chloride or phosgene in the presence of a catalyst such as triethylamine or dimethylformamide at temperature of 60 to 80° C., preferably 70° C. The acid gases ($SO_2$ and HCl) may be removed, together with excess of the chlorinating agent by addition and distillative removal of further organic solvent.

The acid chloride may then be reacted with methane sulphonamide to give fomesafen. This step may suitably be carried out by conventional methods, for example as set out in EP-A-0003416. In a preferred process the acid chloride is coupled with MSAM using an excess of base such as potassium carbonate at 60 to 80° C., preferably at 80° C. The inorganic by-products and excess MSAM are removed by washing with water. The final product solution is topped to remove water. The organic solvent level, in the final product solution, is adjusted by topping off excess or by further additions and the product is then isolated by cooling to −10 to 30° C. preferably 0° C.

A particular advantage in the use of EDC in the coupling reaction with MSAM is that the boiling point of the solvent is the upper temperature limit for process operation and thermal decomposition of the acid chloride during the reaction is avoided.

The product may then be purified using a chloroalkane solvent. The purification may suitably involve filtration and washing with cold solvent or further recrystallisation from the solvent.

Using the process invention, it is possible to obtain fomesafen of desired quality in good yield enabling the industrial operation of the process with a single solvent.

The invention will now be further illustrated with reference to the following examples.

EXAMPLE 1

The Preparation of Fomesafen in EDC

Step A

Extraction of 5-(2-chloro-α,α,α,-trifluoro-4-tolyloxy)-benzoic acid (CTTBA) from the Oxidation Reaction Mass Materials

| Name | Act wt | Str % | 100% wt | Mol Wt | Moles | Mol Ratio |
|---|---|---|---|---|---|---|
| Oxidation mass* | 498.5 | ~50 | 249.3 | 316.5 | 0.788 | — |
| 1,2-dichloroethane (EDC) | 222.3 | 100 | 222.3 | 99 | — | — |
| 1,2-dichloroethane (balance) | 816.6 | 100 | 816.6 | 99 | — | — |
| Water | 475 | 100 | 475 | — | — | — |

*Composition of the topped oxidation mass was:
67% w/w CTTBA intermediate product
7% w/w organic impurities associated with CTTBA
25% w/w acetic acid A 1 lb jar of the oxidation mass containing CTTBA was heated in a water bath to 95° C. to melt the contents of the jar. The molten contents were then charged to a 1 liter jacketed reaction vessel fitted with an anchor agitator, thermometer, Dean & Stark system with condenser and a nitrogen purge applied via a bubbler at the top of the condenser. The reactor had been pre-charged with warm water (475 ml at approx. 50° C.) which was agitated during the addition of the molten batch. The product began to solidify and EDC (175 ml) was charged at which point the deposited solid dissolved and partitioned between the two layers. The reactor contents were heated to approx. 77° C. by external water bath circulation (bath at 80° C.) for 30 minutes before stopping the agitation and allowing the reactor contents to separate. The upper aqueous layer was removed by suction and a warm water wash (506 ml) was charged to the reactor, stirred for 30 minutes and then settled before removing the upper aqueous layer as before. The reactor contents were then heated to reflux to remove residual water. After the system had been azeotropically dried a fixed 'balance' charge of EDC was made to dilute the CTTBA in EDC solution to the safe concentration for the following nitration stage.

| Yield: Product solution weight: | 1326.9 g, |
|---|---|
| Product solution concentration: | 22.1% |
| 100% wt of CTTBA isolated: | 293.1 gm |

Step B
Nitration of CTTBA to Acifluorfen
Materials

| Name | Act wt | Str % | 100% wt | Mol Wt | Moles | Mol Ratio |
|---|---|---|---|---|---|---|
| CTTBA ECD solution | 642.5 | 22.09 | 141.9 | 316.5 | 0.448 | 1.000 |
| Sulphuric acid 98% | 1.81 | 98 | 1.77 | 98 | 0.018 | 0.040 |
| Acetic anhydride | 90.11 | 100 | 90.11 | 102 | 0.883 | 1.972 |
| Mixed acid # | 115.0 | 33 | 37.95 | 63 | 0.602 | 1.345 |

Mixed acid is a mixture of anhydrous nitric acid (33%) and sulphuric acid (67%) by weight.

The CTTBA solution in ECD (prepared as in step A) at 50° C., was charged to a clean dry 1 liter jacketed split reaction vessel fitted with thermometer, turbine agitator, Dean & Stark system fitted with condenser and a nitrogen purge attached via a bubbler to the top of the condenser. The reactor contents were held at 50° C. by jacket circulation and agitated whilst the sulphuric acid was charged. The acetic anhydride was then charged and the reactor contents cooled to 0° C. by applying external cooling to the reactor jacket. On reaching 0° C. the mixed acid was slowly charged to the reactor, using a syringe pump and teflon cannular via a suba seal cap on the reactor, over a period of approximately 2 hrs. During this addition the temperature was controlled at 0–5° C. by periodically stopping the mixed acid addition. A sample was withdrawn for HPLC after a further 15 minute stir to check for completion of nitration—the analysis showed that the reaction was complete and needed no further mixed acid addition. The reaction mass was then quenched with 250 ml of cold water—the temperature rose to approximately 35° C. and the reaction mass allowed to stand overnight without heating or agitation. The following day work-up was effected by agitating the reactor contents whilst heating to 60° C. After an hour stir the agitation was stopped and the two phases allowed to separate. The upper pale yellow aqueous layer was then separated, from the lower red organic layer, by suction. Two further 250 ml cold water washes were then applied, the reactor contents then heated to 60° C., with agitation, and treated in the same manner as the first wash. Residual interfacial material and water stayed with the organic phase after separation and the water was removed by agitating the reactor contents, heating the mixture to reflux via the Dean & Stark facilitating separation of the water and recycling the EDC.

Yield 89.2%

Step C
Chlorination to Acifluorfen Acid Chloride
Materials

| Name | Act wt | Str % | 100% wt | Mol Wt | Moles | Mol Ratio |
|---|---|---|---|---|---|---|
| Acifluorfen EDC solution | 653 | 22.1 | 144.3 | 361.5 | 0.399 | 1.000 |
| Thionyl chloride (initial) | 76.7 | 99 | 75.9 | 119 | 0.638 | 1.600 |
| Thionyl chloride (balance) | 1.63 | 99 | 1.61 | 119 | 0.014 | 0.035 |
| Triethylamine | 0.41 | 99 | 0.4 | 102 | 0.004 | 0.010 |
| ECD purges | 400 ml | — | — | — | — | — |

The acifluorfen in EDC solution at 50° C. was charged to a clean dry 1 liter split reaction vessel fitted with turbine agitator, thermometer, Dean & Stark system fitted with condenser and a nitrogen purge fed in at the top of the condenser via a bubbler. The reactor contents were heated to 70° C. (by external bath heating—bath set at 75° C.) and agitated. The thionyl chloride was then charged, via syringe pump fitted with a Teflon cannular fed in through a suba seal on the reactor, over a period of just under 2 hrs. After complete addition of the thionyl chloride the reactor contents were agitated and heated at 70° C. to ensure complete reaction. A sample of the acid chloride was taken for analysis by GLC. The analysis showed a little unreacted AA was still present—a calculated extra charge of thionyl chloride was added and the reaction heated until all gas evolution stopped. The reaction product obtained contained thionyl chloride, sulphur dioxide and hydrogen chloride gas impurities. In order to remove these impurities two successive additions of EDC were made, each addition being half the volume of the initial product solution, the additional EDC was then removed by distillation.

Yield: 92.6%

Step D
Preparation of Fomesafen from Aciflourfen Acid Chloride
Materials

| Name | Act wt | Str % | 100% wt | Mol Wt | Moles | Mol Ratio |
|---|---|---|---|---|---|---|
| Methanesulphonamide | 11.51 | 99 | 11.39 | 95 | 0.120 | 1.000 |
| EDC | 403.4 | — | — | — | — | — |
| Potassium carbonate | 29.0 | 99 | 28.71 | 138 | 0.208 | 1.734 |
| Acifluorfen acid chloride | 120.3 | 23.54 | 28.22 | 380 | 0.075 | 0.621 |
| EDC for Acifluorfen acid chloride | 70 | — | — | — | — | — |

The methanesulphonamide (MSAM) together with 70 gm of EDC were charged to a clean dry 1 liter jacketed split reaction vessel fitted with a turbine agitator, thermometer, Dean & Stark fitted with condenser and nitrogen purge fed in via a bubbler on the condenser outlet. The mixture was heated up to 80° C. whilst agitating at ~400 rpm. Further EDC was added until the methanesulphonamide had dissolved at 80° C.—a further 403.4 gm. Potassium carbonate was then charged to the reactor and the slurry stirred for a further 1 hr. The required AA acid chloride (prepared as in step C) was then mixed with EDC to dilute to an AA acid chloride concentration of ~17%. The diluted acid chloride solution was then charged to the reactor slurry over ~4 hrs. The reaction mass was adjusted to 55° C., warm water (70 ml) added and the mixture stirred for 30 minutes before stopping the agitation and allowing the two phases to separate. The upper aqueous layer was removed by vacuum. A further warm water wash was then applied (100 ml) stirred for 30 minutes then separated as with the first wash. The reactor contents were then heated up to reflux and were azeotropically dried before the purification stage. The weight of product solution was determined and analysis carried out to determine the fomesafen yield.

Yield: 87.9 %
approximate crude product composition

| | | |
|---|---|---|
| | 2'-nitro | 10.8 pph |
| | 6'-nitro | 5.6 pph |
| | 5-CF$_3$ | 7.3 pph |
| | acifluorfen | 4.3 pph |

Step E
Purification of Fomesafen
Materials

| Name | Act wt | Str % | 100% wt | Mol Wt | Moles | Mol Ratio |
|---|---|---|---|---|---|---|
| fomesafen Crude in EDC | 546.7 | 5.2 | 28.37 | 438.5 | 0.065 | 1.000 |

The EDC solution of crude fomesafen, after azeotrope drying, was held at 80° C. in a 1 liter jacketed reaction vessel fitted with thermometer, turbine agitator, Dean & Stark fitted with condenser and nitrogen purge fed in via a bubbler on the condenser outlet. The reactor contents were agitated at 400 rpm and heated to reflux in order to remove EDC (200 ml removed)—the circulating bath temperature was set to 98° C. to achieve this. In order to obtain purified fomesafen the agitation was reduced to 100 rpm and the solution was cooled in 10° C. steps and holding for 15 minutes for each step, down to a temperature of 0° C. At each step the agitation was stopped and the supernatant mother liquor sampled to determine the product concentration. The reactor contents were then filtered on a sintered nutche and the reactor washed clean with a little cold EDC which was then used to wash the product cake. The product cake was then air dried.

| | |
|---|---|
| Yield: | 82.1% |
| Strength: | 88.8%. |
| approximate crude product composition | |
| 2'-nitro | 0.4 pph |
| 6'-nitro | 0.2 pph |
| 5-CF$_3$ | 2.2 pph |
| acifluorfen | 0.4 pph | where $\text{pph} = \dfrac{\text{parts of impurity}}{\text{parts of fomesafen}} \times \dfrac{100}{1}$ EXAMPLE 2
The Preparation of Fomesafen in Anisole
Step A
Conversion of Acifluourfen to its Acid Chloride A 750 ml split reaction flask fitted with reflux condenser, thermometer, probe for bath controller and nitrogen purge was heated by an external oil bath and connected to a caustic scrubber system. The reactor was charged with acifluorfen (62.0 gm≡0.166 equivalents), dimethyl formamide (0.185 gm≡0.0025 equivalents) and anisole (242 gm). The mixture was heated to 70° C. and agitated. On achieving temperature thionyl chloride (26.4 gm≡0.215 equivalents) was charged over an hour by syringe pump. The reaction was then heated for a further 1.5 hour, after complete addition of the thionyl chloride, to give a clear yellow solution. The reaction mass was then allowed to self cool to 50° C., at which point the apparatus was configured for distillation and a total of 2.5 gm of contaminated anisole (containing thionyl chloride/HCl and SOCl$_2$) was removed (at approx. 50° C. pot temperature and 15 mbar pressure)—distillation was relatively smooth. Vacuum was relieved with nitrogen and the product solution bottled off and analysed by GLC.

Step B
Formation of Crude Fomesafen

A slurry of potassium carbonate (7.8 gm≡0.055 equivalents), anisole (48.6 gm) and Methane Sulphonamide (MSAM 3.22 gm≡0.0322 equivalents) was agitated in a 250 ml split reaction vessel and heated on an oil bath to 70° C. A portion of acifluorfen acid chloride (45 gm @ 22.2%≡0.0263 equivalents) was charged to a syringe pump and then run into the MSAM slurry over a period of approximately 3.5 hours. The reaction was then allowed to stir at 70° C. for 30 minutes then sampled to check for completion of reaction. The reaction was quenched with water (100 gm) and the two phases separated, extra water was required to improve separation. The two layers were then separated and analysed giving a yield of 96.0% as fomesafen in the aqueous phase.

Step C
Purification of Crude Fomesafen

Crude dry fomesafen paste (9.66 gm) was charged, in small portions, to anisole (50 gm) contained in a 100 ml four necked flask fitted with a thermometer and a ptfe paddle agitator. The slurry was agitated and heated, during the addition, with an oil bath to 130° C. Each portion of paste was charged after the previous sample had dissolved. When the system had reached saturation at 130° C. the reaction mass was allowed to self cool and crystallise. The resultant product slurry was filtered off and the paste pulled 'dry' on a nutche before discharging, weighing and analysing.

A grey paste (4.6 gm) of solids 94.3% and strength on dry of 84.3% was obtained giving a yield of 64% based on fomesafen charge.

What is claimed is:

1. A process for producing fomesafen from 5-(2-chloro-α,α,α,-trifluoro-4-tolyloxy-benzoic acid which comprises the steps of:

(i) Extracting 5-(2-chloro-α,α,α,-trifluoro-4-tosyloxy)-benzoic acid from an oxidation reaction mass;

(ii) nitrating 5-(2-chloro-α,α,α,-trifluoro-4-tolyloxy)-benzoic acid to form acifluorfen (iii) converting acifluorfen to its acid chloride (iv) coupling the acid chloride so formed with methane-sulphonamide (MSAM) in the presence a base to form crude fomesafen and (v) purifying the crude fomesafen wherein each of the steps (i) to (iv) is carried out in a single common chloroalkane solvent.

2. A process according to claim 1 wherein the steps are telescoped together so that there is no isolation of the product for any step until fomesafen is obtained.

3. A process according to claim 1 in which the chloroalkane solvent is 1,2-dichloroethane.

4. A process according to claim 1 in which the nitration is performed using a nitrating agent comprising nitric acid or a mixture of nitric and sulphuric acids and in which the reaction takes place in the presence of acetic anhydride, the molar ratio of 5-(2-chloro-α,α,α,-trifluoro-4-tolyloxy) benzoic acid to acetic anhydride being from about 1:1 to 3:1.

5. A process according to claim 1 wherein the 5-(2-chloro-α,α,α,-trifluoro-4-tolyloxy)-benzoic acid is generated by oxidation of the corresponding toluene using oxygen together with a catalyst at a temperature of from 70° C. to 150° C. to form a reaction mass from which the 5-(2-chloro-α,α,α,-trifluoro-4-tolyloxy)-benzoic acid is extracted.

* * * * *

UNITED STATES PATENT AND TRADEMARK OFFICE
CERTIFICATE OF CORRECTION

PATENT NO. : 6,790,991 B2
DATED : September 14, 2004
INVENTOR(S) : Brown et al.

It is certified that error appears in the above-identified patent and that said Letters Patent is hereby corrected as shown below:

Column 9, line 33 through Column 10, line 9,
Claim 1, should read
1. A process for producing fomesafen from 5-(2-chloro-α,α,α,-trifluoro-4-tolyloxy)-benzoic acid which comprises the steps of:
(i) Extracting 5-(2-chloro-α,α,α,-trifluoro-4-tolyloxy)-benzoic acid from an oxidation reaction mass;
(ii) nitrating 5-(2-chloro-α,α,α,-trifluoro-4-tolyloxy)-benzoic acid to form acifluorfen
(iii) converting acifluorfen to its acid chloride
(iv) coupling the acid chloride so formed with methanesulphonamide (MSAM) in the presence of a base to form crude fomesafen and
(v) purifying the crude fomesafen Signed and Sealed this Twenty-fifth Day of January, 2005

JON W. DUDAS
*Director of the United States Patent and Trademark Office*